United States Patent
Pagan et al.

(10) Patent No.: US 12,048,681 B2
(45) Date of Patent: Jul. 30, 2024

(54) COMPOSITIONS AND METHODS FOR MODULATING EQUINE FATTY ACID PROFILES

(71) Applicant: KENTUCKY EQUINE RESEARCH, INC., Versailles, KY (US)

(72) Inventors: Joe D. Pagan, Versailles, KY (US); Ashlee Hauss, Versailles, KY (US)

(73) Assignee: KENTUCKY EQUINE RESEARCH, INC., Versailles, KY (US)

( * ) Notice: Subject to any disclaimer, the term of this patent is extended or adjusted under 35 U.S.C. 154(b) by 0 days.

(21) Appl. No.: 17/884,120

(22) Filed: Aug. 9, 2022

(65) Prior Publication Data

US 2023/0059473 A1 Feb. 23, 2023

Related U.S. Application Data

(60) Provisional application No. 63/230,949, filed on Aug. 9, 2021.

(51) Int. Cl.
*A61K 31/202* (2006.01)
*A61P 1/04* (2006.01)
*A61P 29/00* (2006.01)

(52) U.S. Cl.
CPC ............. *A61K 31/202* (2013.01); *A61P 1/04* (2018.01); *A61P 29/00* (2018.01)

(58) Field of Classification Search
CPC ........... A61K 31/202; A61P 1/04; A61P 29/00
See application file for complete search history.

(56) References Cited

U.S. PATENT DOCUMENTS

| | | |
|---|---|---|
| 5,246,726 A | 9/1993 | Horrobin et al. |
| 5,709,855 A | 1/1998 | Bockow |
| 8,716,332 B2 | 5/2014 | Fulgham |
| 9,222,112 B2 | 12/2015 | Apt et al. |

(Continued)

FOREIGN PATENT DOCUMENTS

| | | | | |
|---|---|---|---|---|
| CA | 2904112 C | * | 3/2021 | ............. A61K 31/20 |
| EP | 0347056 B1 | | 4/1993 | |
| WO | 88/02221 A1 | | 4/1988 | |

OTHER PUBLICATIONS

King SS, Abughazaleh AA, Webel SK, Jones KL. Circulating fatty acid profiles in response to three levels of dietary omega-3 fatty acid supplementation in horses. J Anim Sci. 2008;86, 1114-1123.

(Continued)

*Primary Examiner* — Deborah D Carr
(74) *Attorney, Agent, or Firm* — Stites & Harbison, PLLC; Terry L. Wright

(57) ABSTRACT

A composition is provided comprising an effective amount of a combination of gamma linolenic acid (GLA), docosahexaenoic acid (DHA), and eicosapentaenoic acid (EPA). The composition comprises about 5% w/w to about 25% w/w GLA, and about 5% w/w to about 25% w/w of a mixture of DHA and EPA. Methods of modulating fatty acid profiles or treating an inflammatory condition in a horse include administering an effective amount of the composition to the horse. The inflammatory conditions capable of being treated include gastric ulcers, airway inflammation, joint inflammation, or combinations thereof.

8 Claims, 8 Drawing Sheets

(56) References Cited

U.S. PATENT DOCUMENTS

2012/0252888 A1* 10/2012 Pantzaris ............ A61K 31/202
514/458
2012/0309831 A1 12/2012 Van Anholt et al.
2016/0015666 A1 1/2016 Burattin

OTHER PUBLICATIONS

Vineyard KR, Warren LK, Kivipelto J. Effect of dietary omega-3 fatty acid source on plasma and red blood cell membrane composition and immune function in yearling horses. J Anim Sci. 2010;88:248-257. https://doi.org/10.2527/jas.2009-2253.

Hess TM, Rexford JK, Hansen DK, et al. Effects of two different dietary sources of long chain omega-3, highly unsaturated fatty acids on incorporation into the plasma, red blood cell, and skeletal muscle in horses. J Anim Sci. 2012;90,3023-3031.

Hess T, Braun, S, Herkelman, K. The effects of various levels of docosahexaenoic acid on inflammatory markers in conditioned horses during lactate threshold tests. J Equine Vet Sci. 2019;72:64-71.

Harris WS, Varvel SA, Pottala JV, Warnick GR, McConnell JP. Comparative effects of an acute dose of fish oil on omega-3 fatty acid levels in red blood cells versus plasma: implications for clinical utility. J Clin Lipidol. 2013;7(5) 433-440.

Nogradi N, Couetil LL, Messick J, Stochelski MA, Burgess JR. Omega-3 fatty acid supplementation provides an additional benefit to a low-dust diet in the management of horses with chronic lower airway inflammatory disease. J Vet Intern Med. 2015;29, 299-306.

Gurzell EA, Wiesinger J, Morkam C, Hemmrich S, Harris W, Fenton J. Is the omega-3 index a valid marker of intestinal membrane phospholipid EPA+DHA content? Prostaglandins Leukot Essent Fatty Acids. 2014;91(3):87-96.

United States Patent and Trademark Office, International Search Report and Written Opinion issued in corresponding Application No. PCT/US2022/039815, mailed Dec. 30, 2022.

Alammar, WA., et al. "Effect of omega-3 fatty acids and fish oil supplementation on multiple sclerosis: a systematic review"; Nutritional Neuroscience, vol. 24, Issue 11 (Aug. 2019), pp. 1-11.

* cited by examiner

*** different from month 0 (p<.001)

COMPOSITIONS AND METHODS FOR MODULATING EQUINE FATTY ACID PROFILES

RELATED APPLICATIONS

This application claims priority from U.S. Provisional Application Ser. No. 63/230,949, filed Aug. 9, 2021, the entire disclosure of which is incorporated herein by this reference.

TECHNICAL FIELD

The presently-disclosed subject matter generally relates to compositions and methods for modulating equine fatty acid profiles. In particular, certain embodiments of the presently-disclosed subject matter relate to compositions and methods for modulating equine fatty acid profiles that make use of various combinations and concentrations of omega-3 and omega-6 fatty acids.

BACKGROUND

Modern equine diets tend to provide a skewed ratio of omega-3 and omega-6 fatty acids, with most equine diets underproviding omega-3s and oversupplying omega-6s. Cereal grains such as oats and corn, as well as many vegetable oils, are high in omega-6s, while hay and pasture provide omega-3s, despite being low in total fat content. Canola and soy oil have an adequate omega-3 content, though still lower than the amount of omega-6 provided.

Too many omega-6s and too few omega-3s can result in excessive inflammation in the body. Therefore, having adequate amounts of omega-3s in the diet to moderate the pro-inflammatory response of the omega-6s has generally been regarded as desirable. Some of the most useful omega-3 fatty acids for conferring health benefits that have been identified to date are docosahexaenoic acid (DHA) and eicosapentaenoic acid (EPA), as they have higher biological activity. Indeed, optimal levels of such omega-3 fatty acids have been shown to reduce body-wide inflammation and to support immune function with specific applications for allergies, skin conditions, respiratory issues, and joint health. Reproductive benefits of the omega-3 fatty acids include improved fertility, enriched colostrum quality, enhanced passive transfer of antibodies to foals, and increased sperm concentration, motility, and viability.

There are three main forms of omega-3s: alpha-linolenic acid (ALA), eicosapentaenoic acid (EPA), and docosahexaenoic acid (DHA). The parent omega-3 ALA is generally regarded as being essential in the diet, meaning the body cannot make it on its own. The body converts ALA into EPA and DHA, but this process is inefficient in mammals. For this reason, finding a good source of dietary EPA and DHA is helpful for increasing omega-3 fatty acids in the body. However, it is also important to balance omega-3 fatty acid intake with that of omega-6, as the two work together for proper immune function and cell membrane structure. As such, compositions and methods for improving the balance of omega-3 and omega-6 fatty acids and, more particularly, improving or modulating the fatty acid profiles in horses would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes, in some embodiments, compositions and methods for modulating equine fatty acid profiles that make use of various combinations and concentrations of omega-3 and omega-6 fatty acids. In some embodiments, a composition is provided that comprises an effective amount of a combination of gamma linolenic acid (GLA), docosahexaenoic acid (DHA), and eicosapentaenoic acid (EPA). In some embodiments, the composition comprises about 5% w/w to about 25% w/w GLA or about 5% w/w to about 10% w/w GLA. In some embodiments, the composition comprises about 5% w/w to about 25% w/w of a mixture of DHA and EPA or about 5% w/w to about 15% w/w of a mixture of DHA and EPA. In some embodiments, the composition comprises about 5% w/w to about 25% w/w GLA, and about 5% w/w to about 25% w/w of a mixture of DHA and EPA, such as, in certain embodiments, about 10% w/w GLA and about 21% w/w of a mixture of DHA and EPA or, in other embodiments, about 5% w/w GLA and about 25% w/w of a mixture of DHA and EPA.

In some embodiments of the presently-disclosed subject matter, a composition is provided that comprises an effective amount of a combination of GLA, DHA, and EPA, where the DHA and EPA is included in the composition as a mixture of DHA and EPA, and where the GLA is included in the composition at a ratio of about 0.25-2.5 parts GLA to about 1 part of the mixture of DHA and EPA. In some embodiments, the ratio of GLA to the mixture of DHA and EPA is in a range of about 0.5:1 to about 1.5:1.

Further provided, in some embodiments, are methods of modulating fatty acid profiles. In some embodiments, a method of modulating fatty acid profiles in a horse is provided that comprises administering to the subject an effective amount of a composition including a combination of GLA, DHA, and EPA. In some implementations of the method of modulating fatty acid profiles, the composition comprises about 5% w/w to about 25% w/w GLA, and about 5% w/w to about 25% w/w of a mixture of DHA and EPA. In some implementations, administering the composition increases an amount of EPA, DHA, GLA, and/or dihomo-gamma-linolenic acid (DGLA) in a biological sample obtained from the horse. Such biological samples can comprise plasma or red blood cells and, in certain embodiments, the EPA, DHA, GLA, and/or DGLA is incorporated into the cell membranes of the red blood cells. In some implementations, administering the composition comprises administering an amount sufficient to increase an amount of GLA and/or DGLA in the horse and/or to reduce an amount of or incidence of gastric ulcers, airway inflammation, or joint inflammation in the horse.

Still further provided, in some embodiments, are methods of treating an inflammatory condition in a horse that include administering an effective amount of a composition of the presently disclosed subject matter (e.g., a composition comprising about 5% w/w to about 25% w/w GLA, and about 5% w/w to about 25% w/w of a mixture of DHA and EPA). In some implementations, the inflammatory condition is selected from the group consisting of a gastric ulcer, airway inflammation, joint inflammation, or combinations thereof. In some implementations, administering an effective amount of the composition comprises administering an amount of the composition sufficient to decrease an amount of an inflammatory cytokine, such as interleukin (IL)-8, and increase an amount of an anti-inflammatory cytokine, such as IL-10, in the horse.

Further features and advantages of the present invention will become evident to those of ordinary skill in the art after a study of the description, figures, and non-limiting examples in this document.

DESCRIPTION OF EXEMPLARY EMBODIMENTS

Figure 1:
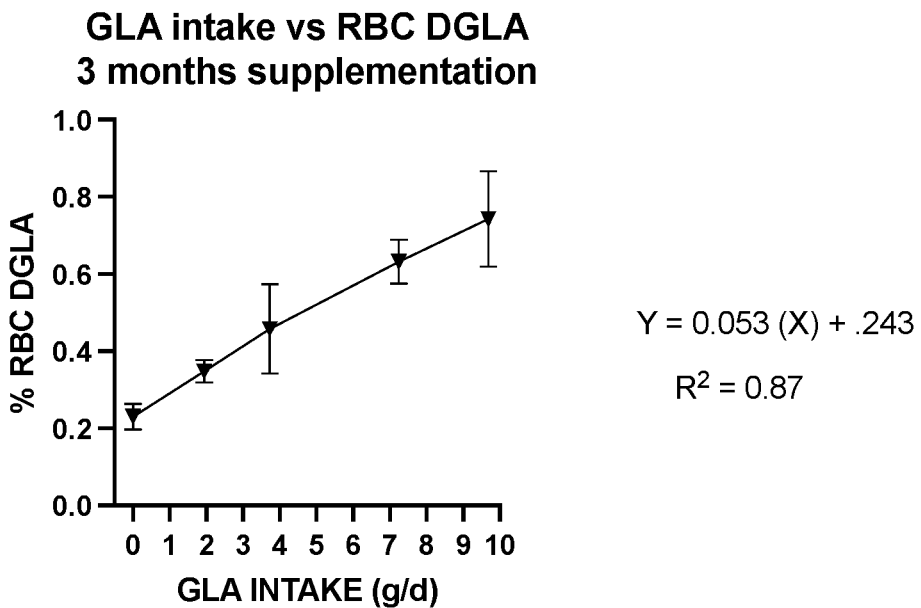
FIG. 1 is a graph showing gamma linolenic acid (GLA) intake versus the percent of dihomo-gamma linolenic acid (DGLA) content in red blood cells (RBCs) after three months of supplementation.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Where reference is made to a URL or other such identifier or address, it is understood that such identifiers can change and particular information on the internet can come and go, but equivalent information can be found by searching the internet. Reference thereto evidences the availability and public dissemination of such information.

As used herein, the abbreviations for any protective groups, fatty acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is based, at least in part, on the discovery that while horses are not able to effectively elongate the short-chain polyunsaturated fatty acids (SC-PUFA) alpha-linolenic acid (ALA) or linoleic acid (LA) obtained through dietary sources into long-chain polyunsaturated fatty acids (LC-PUFA), such as docosahexaenoic acid (DHA), eicosapentaenoic acid (EPA), and dihomo gamma linolenic acid (DGLA), direct supplementation with combinations of LC-PUFA omega-3 and specific SC-PUFA omega-6 fatty acids, including particular concentrations of DHA, EPA, and gamma linolenic acid (GLA), resulted in increased levels of the fatty acids EPA, DHA, and DGLA in plasma and red blood cells (RBCs). Moreover, the increased levels of the LC-PUFAs led to reductions in the incidence of gastric ulcers, lower heart rates and evidence of respiratory bleeding with intense exercise, as well as improved airway inflammation and inflammatory response following exercise stress. As such, in some embodiments, the presently-disclosed subject matter thus includes compositions and methods that make use of various combinations and concentrations of LC-PUFA omega-3 and SC-PUFA omega-6 fatty acids for modulating equine fatty acid profiles and treating various inflammatory conditions.

As used herein, the phrase "omega-3 fatty acids," which may also be referred to as omega-3 oils, ω-3 fatty acids, or n-3 fatty acids, is used to refer to polyunsaturated fatty acids (PUFAs) that are characterized by the presence of a double bond, three atoms away from the terminal methyl group in their chemical structure. As would be recognized by those skilled in the art, such omega-3 fatty acids include, but are not limited to, the short-chain polyunsaturated fatty acid (SC-PUFA) alpha-linolenic acid (ALA) (C18:3n3) or long-chain polyunsaturated fatty acids (LC-PUFAs) such as eicosapentaenoic acid (EPA) (C20:5n3) and docosahexaenoic acid (DHA) (C22:6n3).

Similarly, the phrase "omega-6 fatty acids," which is sometimes used interchangeably with the phrases ω-6 fatty acids, n-6 fatty acids, or the like is used herein to refer to members of the family of polyunsaturated fatty acids that have a final carbon-carbon double bond in the n-6 position, that is, the sixth bond, counting from the methyl end. Such omega-6 fatty acids include, but are not limited to, short-chain polyunsaturated fatty acids (SC-PUFAs) such as linoleic acid (LA)(C18:2n6) and gamma linolenic acid (GLA) (C18:3n6), or long-chain polyunsaturated fatty acids (LC-PUFAs) such as dihomo-gamma-linolenic acid (DGLA) (C20:3n6) and arachidonic acid (AA)(C20:4n6).

In some embodiments of the presently-disclosed subject matter, a composition is provided that comprises an effective amount of a combination of gamma linolenic acid (GLA), docosahexaenoic acid (DHA), and eicosapentaenoic acid (EPA). In some embodiments, it has been observed that the amounts, including the concentrations, of these fatty acids can be included in a composition of the presently-disclosed subject matter so as to provide a desired modulation of the fatty acid profile in a horse administered the compositions.

For instance, in some embodiments of the compositions, and with respect to the GLA included in an exemplary compositions, the composition comprises about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% w/w GLA. In some embodiments, the composition comprises about 5% w/w to about 25% w/w GLA, including, in certain embodiments, about 5% w/w to about 10% w/w GLA.

As another example, in some embodiments, and with respect to the DHA and EPA included in an exemplary composition, the composition comprises about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% w/w of a mixture of DHA and EPA. In some embodiments, the composition comprises about 5% w/w to about 25% w/w of a mixture of DHA and EPA, including, in some embodiments, about 5% w/w to about 15% w/w of a mixture of DHA and EPA. In some embodiments, the EPA and DHA included in the mixture of EPA and DHA is included at a EPA:DHA ratio of about 1:1, about 1:2, about 1:3, about 1:4, and about 1:5.

In some further embodiments of the presently-disclosed subject matter, the GLA is combined with the DHA and EPA in a composition to provide a desired mixture of the omega-3 and omega-6 fatty acids as a means to provide a desired balance and/or modulation of the activity and effects of those fatty acids. In some embodiments, the composition comprises about 5% w/w to about 25% w/w GLA, and about 5% w/w to about 25% w/w of DHA+EPA. In other embodiments, the composition comprises about 10% w/w GLA and about 10% w/w DHA+EPA. In some further embodiments, the composition comprises about 5% w/w GLA and about 15% w/w DHA+EPA.

In some further embodiments of the presently-disclosed subject matter, rather than expressing the components of the compositions as a weight concentration of the components included in the composition (e.g., % w/w), a composition is provided in which the GLA is included in an amount or ratio relative to the amount of DHA and EPA (i.e., DHA+EPA) included in the composition. In some embodiments, a composition is provided in which the amount of GLA to EPA and DHA is included in the composition at a ratio of GLA to EPA and DHA (i.e., GLA:EPA+DHA) of about 0.25:1 to about 2.5:1 (i.e., 0.25-2.5:1 of GLA:EPA+DHA). In some embodiments the ratio of GLA:EPA+DHA is about 0.5-1.5:1.

In still further embodiments of the presently-disclosed subject matter, and as described in further detail below, the amount of GLA in combination with DHA and EPA is included in an exemplary composition to provide for a daily intake of GLA in combination with a mixture of DHA and EPA sufficient to produce a desired response in a horse (e.g., a modulation in fatty acid profiles). In some embodiments, a composition is thus provided that includes GLA in an amount sufficient to provide for a daily intake of 1 g/d to 10 g/d GLA and that further includes a combination of EPA and DHA in an amount sufficient to provide for a daily intake of 5 g/d to 15 g/d of a mixture of EPA and DHA.

To produce a composition in accordance with the presently-disclosed subject matter (e.g., a composition including GLA in combination with EPA and DHA), the GLA included in the exemplary composition may be obtained from naturally-occurring sources, including, but not limited to sources such as borage oil, black currant oil, and evening primrose oil, as well as highly concentrated GLA safflower oil or other purified sources of GLA. Similarly, in the compositions of the presently-disclosed subject matter, the EPA and DHA included in an exemplary composition can be obtained from sources such as fish oil, algae, and other marine sources, but it is further contemplated that synthetic sources of EPA and/or DHA can be utilized as well. Regardless of the particular source, however, the GLA, EPA, and DHA included in the compositions, including the sources of those compositions, can then be blended together with an appropriate diluent to satisfy a daily intake and/or specific dose requirement using diluents and methods known to those skilled in the art.

In some embodiments, as an alternative to including only GLA in a composition of the presently-disclosed subject matter, DGLA is instead included in an exemplary composition, either alone or in combination with GLA. In such compositions, the amount of DGLA and, if present, GLA included in the composition is sufficient to provide about 1 d/g to 10 g/d of DGLA alone or in combination with GLA. In some embodiments of such compositions, a composition is provided in which DGLA and GLA (if present) is included in a ratio of 0.25-2.5:1 EPA and DHA (i.e., a ratio of 0.25-2.5:1 GLA+DGLA:EPA+DHA).

Further provided, in some embodiments of the present-disclosed subject matter, are methods of modulating fatty acid profiles in a horse or, in other words, modulating the balance between the amounts and types of omega-3 and omega-6 fatty acids present in the horse. In some embodiments, a method of modulating fatty acid profiles in a horse is provided that comprises administering to the horse an effective amount of a composition of the presently-disclosed subject matter that includes a combination of an amount of gamma linolenic acid (GLA), an amount of docosahexaenoic acid (DHA), and an amount of eicosapentaenoic acid (EPA).

The term "modulate" as used herein in relation to the modulation of fatty acid profiles in a target subject is used to refer to varying or changing the fatty acid profiles of a subject, including both increasing and/or decreasing the amounts or balance of omega-3 and omega-6 fatty acids in a subject. In this regard, the skilled artisan will understand that the terms "modulate," "increase," "decrease," and the like do not necessarily refer to an entire alteration of a fatty acid profile or other factor in a subject, but can instead be determined relative to a control, wherein the control can be representative of a subject or environment in which a composition of the presently-disclosed subject matter is not administered or is administered at a particular level. For example, in some embodiments, a modulation in a fatty acid profile relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% increase or decrease in a level of a particular omega-3 or omega-6 fatty acid, or in a level of longer-chain fatty acid produced from the administered shorter-chain fatty acids (e.g., a change in DGLA from GLA). In some embodiments, the increases and/or decreases described herein can be in reference to a control subject that has not been treated with one of the presently-disclosed compositions. In other embodiments, the increases and/or decreases described herein can be in reference to a baseline obtained in a subject that is in need of treatment, but has not yet begun a particular therapeutic regimen with the compositions described herein.

For administration of a therapeutic composition as disclosed herein, in some embodiments, the amounts administered can be expressed as grams administered per day or g/d. In some embodiments, the amounts of the fatty acids included in the compositions described herein are administered in the range of about 1 g/d to about 15 g/d to achieve the desired response or modulation. For example, in some embodiments, the amount of a mixture of EPA and DHA administered is in the range of about 1 g/d to about 20 g/d, while the amount of GLA administered is in the range of about 1 g/d to about 15 g/d. In some embodiments, the GLA is administered at about 1 g/d to about 10 g/d, while the mixture of DHA and EPA is administered at about 5 g/d to about 15 g/d. In some embodiments, the GLA is administered at about 3 g/d to about 7 g/d, while the mixture of DHA and EPA is administered at about 7 g/d to about 12 g/d.

The compositions of the presently-disclosed subject matter are typically administered as an oral supplement and are thus generally administered to horses orally as a top-dressing or dietary treatment on a desired food source (e.g., grain). It is contemplated, however, that suitable methods for administering a composition in accordance with the methods of the presently-disclosed subject matter can also include, but are not limited to, systemic administration, parenteral administration (including intravascular, intramuscular, and/or intraarterial administration), buccal delivery, rectal delivery, subcutaneous administration, intraperitoneal administration, inhalation, intratracheal installation, surgical implantation, transdermal delivery, local injection, intranasal delivery, and hyper-velocity injection/bombardment. In some embodiments, the administration of the composition is via oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof.

Regardless of the route of administration, the compositions of the presently-disclosed subject matter are typically administered in an amount effective to achieve the desired response. As such, the term "effective amount" is used herein to refer to an amount of the therapeutic composition (e.g., a composition comprising an amount of DHA, EPA, and GLA) sufficient to produce a measurable biological response (e.g., a change in a fatty acid profile). Actual dosage levels of active ingredients in a composition of the presently-disclosed subject matter can be varied so as to administer an amount of the active compound(s) that is effective to achieve the desired therapeutic response for a particular horse and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the horse being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's: The Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

In some embodiments, and as noted above, administering the composition increases an amount of EPA, DHA, GLA, and/or dihomo-gamma-linolenic acid (DGLA) in a horse, including in a biological sample obtained from the horse. In this regard, the term "biological sample" as used herein thus refers to any body fluid or tissue potentially comprising a fatty acid. In some embodiments, for example, the biological sample can be a blood sample, a serum sample, a plasma sample, or subfractions thereof. In some embodiments, the biological sample comprises plasma or red blood cells. In some embodiments, the biological sample comprises red blood cells, and the EPA, DHA, GLA, and/or DGLA is incorporated into the cell membranes of the red blood cells.

Turning now to the step of measuring the fatty acid profile in a horse, including identifying an amount of omega-3 and/or omega-6 fatty acids present in a horse, various methods known to those skilled in the art can be used to identify the fatty acids in the provided biological sample. For instance, in some embodiments, the amount of DHA, EPA, GLA, and/or DGLA can be measured in a biological sample obtained from a subject using standard gas chromatography techniques.

In some further embodiments, by virtue of modulating the fatty acid profiles in a subject (e.g., a horse), the fatty acid profiles in a subject can be improved such that the administration of the composition can be used to alleviate or treat one or more inflammatory conditions in the subject, such as reducing an amount of or incidence of gastric ulcers, airway inflammation, and/or joint inflammation in the horse. As such, further provided in some embodiments of the presently-disclosed subject matter are methods of treating an inflammatory condition in a horse that includes administering an effective amount of a composition of the presently-disclosed subject matter (e.g., a composition including an effective amount of a combination of DHA, EPA, and GLA).

The terms "treatment" or "treating," as used herein, refer to the medical management of a subject with the intent to modulate, cure, ameliorate, stabilize, or reduce the occurrence of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; treatment directed to minimizing or partially or completely inhibiting the development of the associated disease, pathological condition, or disorder; and supportive treatment, that is, treatment employed to supplement another therapy directed toward the improvement of the associated disease, pathological condition, or disorder. In some embodiments, the subject is known to have or currently be suffering from a particular condition (e.g., gastric ulcers), while in other embodiments, the subject may be at a risk of suffering from such a condition.

As used herein, the term "inflammatory condition" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents or conditions. Such inflammatory conditions include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include capable of treatment with the presently-disclosed compositions include, in some embodiments, gastric ulcers, airway inflammation, and/or joint inflammation, and may be diagnosed or assessed by standard methods known to those skilled in the art of medicine, including veterinary medicine.

With further respect to the therapeutic methods described herein, including the above-described methods of treating an inflammatory conditions, in some embodiments of the therapeutic methods, administering a composition of the presently-disclosed subject matter reduces an amount of an inflammatory cytokine and/or increases an amount of an anti-inflammatory cytokine in a subject. In some embodiments, administering the composition reduces an amount of IL-8 (inflammatory cytokine) in a subject and/or increases an amount of IL-10 (anti-inflammatory cytokine) in the subject.

Various methods known to those skilled in the art can also be used to determine a reduction in the amount of an inflammatory cytokine in a subject such as a horse. For example, in certain embodiments, the amounts of expression of an inflammatory cytokine in a subject can be determined by probing for mRNA of the gene encoding the inflammatory cytokine in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, CA). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

With further regard to determining levels of an inflammatory cytokine in samples, mass spectrometry and/or immunoassay devices and methods can also be used to measure the inflammatory cytokine in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various methods described herein, although certain embodiments of the methods disclosed herein only call for a qualitative assessment (e.g., the presence or absence of the expression of an inflammatory cytokine in a subject), other embodiments of the methods call for a quantitative assessment (e.g., an amount of a reduction in the level of an inflammatory cytokine in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of an inflammatory cytokine in a subject can be compared to control level of an inflammatory cytokine, and an amount of an inflammatory cytokine of less than or equal to the control level can be indicative of a reduction in the amount of inflammatory cytokines, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Finally, while the compositions and methods described herein have been described with particular reference to horses, it is contemplated that the present compositions and methods can be performed on a wide variety of subjects. Indeed, the term "subject" as used herein is not particularly limited. The term "subject" is inclusive of vertebrates, such as mammals, and the term "subject" can include human and veterinary subjects. Thus, the subject of the herein disclosed methods can be a human, non-human primate, horse, pig, rabbit, dog, sheep, goat, cow, camel, cat, guinea pig, rodent, or the like. The term does not denote a particular age or sex. Thus, adult and newborn subjects, as well as fetuses, whether male or female, are intended to be covered.

The presently-disclosed subject matter is further illustrated by the following specific but non-limiting examples. The following examples may include compilations of data that are representative of data gathered at various times during the course of development and experimentation related to the present invention.

EXAMPLES

Example 1—Analysis of the Effect of Varied Levels of Omega-3 and Omega-6 Oil Supplementation on Plasma and RBC Fatty Acid Content Materials & Methods Twenty-three Thoroughbred horses (aged 4 to 19 years) were used in a longitudinal design to study how supplementation of varied levels of EPA, DHA, and GLA impact the equine blood fatty acid profile. Dietary treatments included no supplementation (control) or oil supplementation at different levels of EPA, DHA, and GLA top-dressed on grain concentrate twice daily for three months. Horses were assigned one of five treatments (4 horses per treatment; Table 1) for three months and were followed an additional three months after cessation of supplementation. Fatty acid composition of plasma and red blood cell (RBC) was measured monthly from July to December.

Horses were subjected to varied management practices from full-time pasture turnout with no exercise to horses stalled and in consistent exercise work six days per week. Horses received varied amounts and types of grain concentrate and hay. They also had widely variable access to fresh grass pasture (4-24 h/d).

TABLE 1

Treatment compositions.

| TRT No. | n | Fatty Acid Supply | GLA (g/d) | EPA + DHA (g/d) |
|---|---|---|---|---|
| 1 | 4 | 22.5% GLA | 9.690 | .001 |
| 2 | 4 | 20% GLA | 7.251 | .109 |
| 3 | 4 | 10% GLA with EPA + DHA (0.86:1 GLA: EPA + DHA) | 3.732 | 4.315 |
| 4 | 4 | 5% GLA with EPA + DHA (0.30:1 GLA: EPA + DHA) | 1.946 | 6.434 |
| 5 | 4 | None | — | — |

Results

Direct supplementation with GLA, EPA, and/or DHA modified the fatty acid profile of equine plasma and red blood cells (RBCs). There was a consistent dose response (FIGS. 1-2) to supplementation of all three fatty acids. Varied management styles and intakes of grain, hay, and fresh grass did not affect the ability for supplemental EPA, DHA, and GLA to alter the equine blood fatty acid profile. Additionally, fresh grass access high in ALA and LA did not seem to impact fatty acid changes in any of the longer-chain fatty acids EPA, DHA, and GLA. Horses were not able to effectively elongate ALA or LA into these longer-chain fatty acids. These results supported the need for direct supplementation in order to increase levels of these fatty acids in plasma and RBCs.

Figure 2:
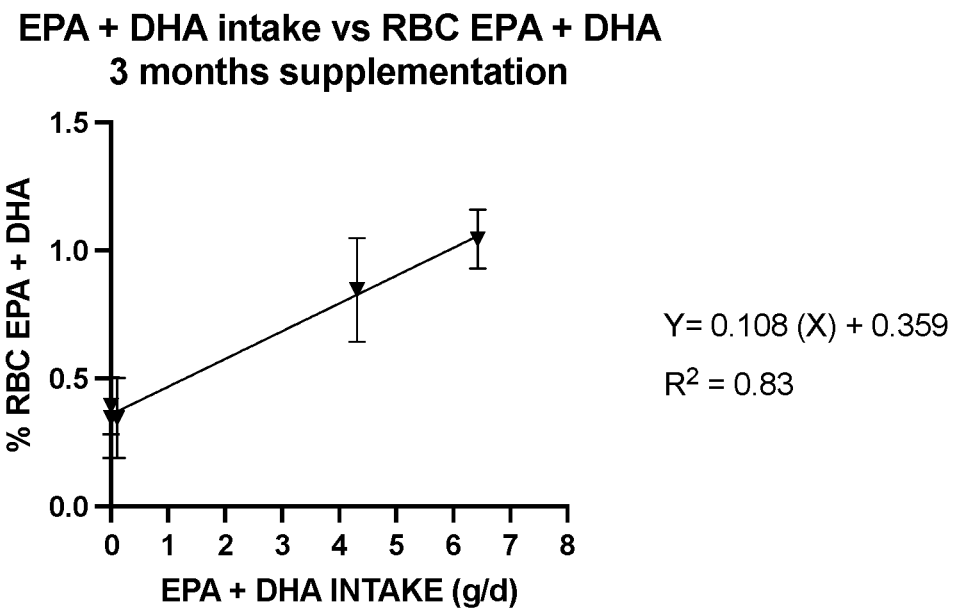
FIG. 2 is a graph showing eicosapentaenoic acid (EPA) and docosahexaenoic acid (DHA) intake versus the percent of EPA and DHA content in red blood cells (RBCs) after three months of supplementation.

There was a strong positive linear relationship ($R^2=0.87$) between GLA intake and RBC DGLA incorporation after 90 days of supplementation (FIG. 1). As GLA intake increased, more DGLA was incorporated into RBCs. This illustrated horses can effectively convert GLA to DGLA and indicated an important dose response. Intake levels of EPA and DHA responded similarly against incorporation of EPA and DHA into RBCs (FIG. 2; $R^2=0.83$). Significantly, when not supplemented with EPA and DHA (data not shown, intake of 0), there was a loss of EPA and DHA incorporated into RBCs.

Figure 3:
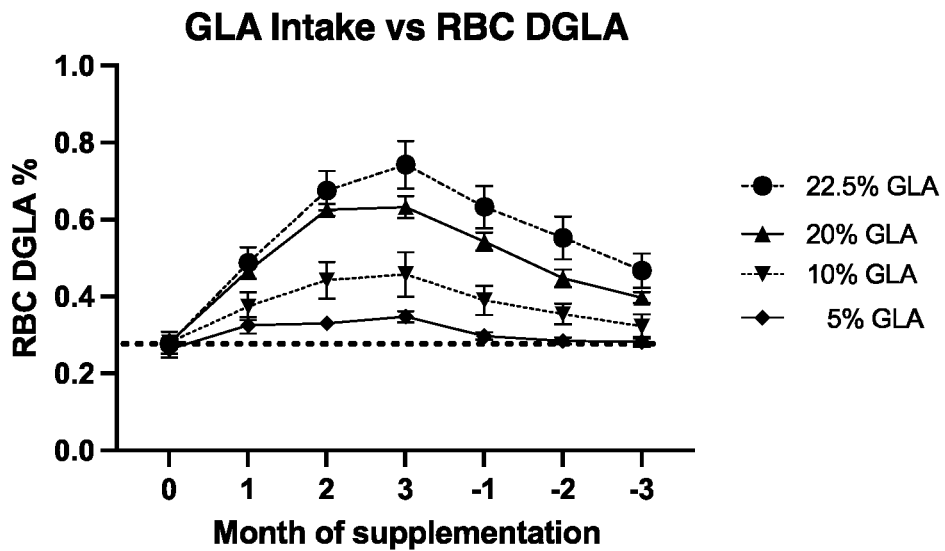
FIG. 3 is a graph showing the change in DGLA content of RBCs over time following GLA supplementation.

The highest level of GLA supplementation (22.5% GLA) was able to incorporate the most DGLA into RBCs by three months of supplementation before potentially reaching maximal change (FIG. 3). This level also took longer to reduce after cessation of supplementation. Results further indicated that higher levels of supplementation take longer to elicit maximal changes and more time to washout.

In summary, the above-described studies showcased clear and distinct manipulation of equine plasma and RBC fatty acid composition depending on levels of direct supplementation with GLA, EPA, or DHA. Supplying longer-chain fatty acids directly allowed the horse to avoid minimally effective and competitive elongation steps. A preferred equine fatty acid profile, however, was not determined in these initial studies and thus further research was undertaken to determine what beneficial physiological changes can result from an altered fatty acid profile supported by a specific proprietary ratio of GLA, EPA, and DHA.

Example 2—Assessment of Physiological Response to GLA, EPA, and DHA Supplementation in Intensely-Exercised Thoroughbreds Materials & Methods Thirteen physically fit Thoroughbred horses of racing age (aged 2 to 8 years) were used in a crossover design to study the effects of supplementing long-chain anti-inflammatory omega-3 fatty acids EPA and DHA and a specific SC-PUFA omega-6 fatty acid GLA on physiological responses in intensely exercised racehorses. Horses underwent baseline testing prior to supplementation and were split into two groups balanced for age, gender, bodyweight, breeze speed, ulcer score, gastric pH, and RBC count. Groups were supplemented with a blend of GLA, EPA and DHA (GLA-EPA-DHA; n=13) or a blend of LA and ALA (LA-ALA; n=13). These treatments provided similar daily intakes of omega-3 and omega-6 fatty acids but at different fatty acid lengths. GLA-EPA-DHA provided longer-chain fatty acids while the LA-ALA blend provided the shorter-chain parent fatty acids. Horses were supplemented twice daily for three months on one treatment before switching treatments for another three months. Horses were in intense exercise training throughout the trial consisting of galloping three days per week on a dirt racetrack and walking 30 min per day on a mechanical exerciser three days per week. Fatty acid composition of plasma and red blood cells (RBC) were measured monthly. Prior to supplementation and at the end of each treatment period, horses underwent a series of collection procedures. Blood, bronchoalveolar lavage (BAL) fluid, gastric fluid, muscle biopsies, and radiographs were collected around or after breezing (14-16 m/s) for three furlongs on a dirt racetrack. At minimum, measurements were collected for assessment of exercise-induced pulmonary hemorrhage (EIPH), ulcer score, gastric pH, mitochondrial respiration, and inflammatory cytokines.

The daily intake of 60 ml/d of GLA-EPA-DHA oil supplied 9.0 g of omega-3 fatty acids consisting mainly of eicosapentaenoic acid (EPA) (C20:5n3) and docosahexaenoic acid (DHA) (C22:6n3), while 35 ml/d of LA-ALA oil supplied 10.2 g of omega-3 fatty acids as alpha-linolenic acid (ALA) (C18:3n3).

The GLA-EPA-DHA and LA-ALA oil blends provided 8.2 g and 8.0 g of omega-6 fatty acids, respectively. All of the omega-6 fatty acid in the LA-ALA oil blend was linoleic acid (LA)(C18:2n6), while 5.4 g of the GLA-EPA-DHA oil blend was supplied as gamma linolenic acid (GLA)(C18: 3n6) and 2.5 g was linoleic acid (LA)(C18:2n6).

TABLE 2

Daily Intake of Fatty Acids with Supplementation.

| Fatty Acid | LA-ALA supplement (g/d) | GLA-EPA-DHA supplement (g/d) |
|---|---|---|
| LA | 8.0 | 2.5 |
| ALA | 10.2 | 0 |
| GLA | 0 | 5.4 |
| AA | 0 | 0.3 |
| EPA | 0 | 4.4 |
| DPA | 0 | 0.8 |
| DHA | 0 | 3.8 |
| EPA + DHA | 0 | 8.2 |
| OMEGA 3 | 10.2 | 9.0 |
| OMEGA 6 | 8.0 | 8.2 |

Results

Figure 4:
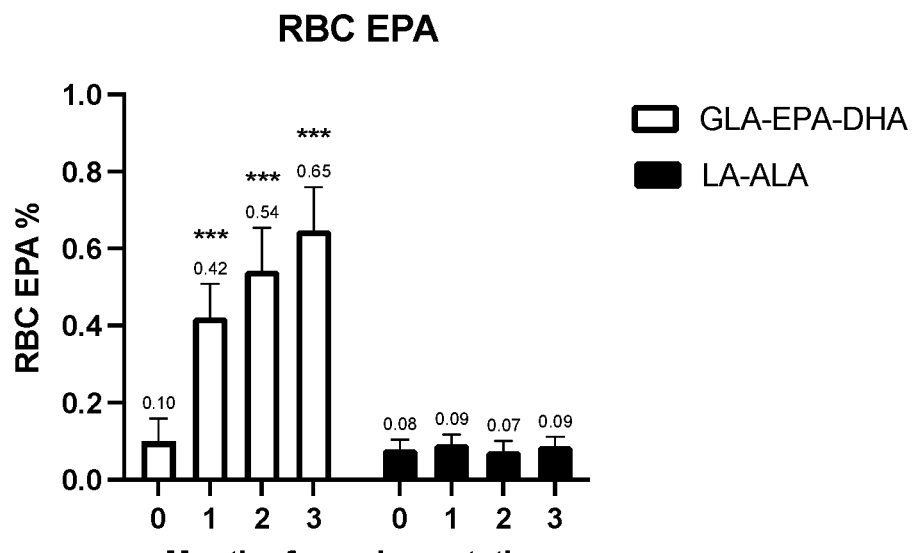
FIG. 4 is a graph showing EPA content of RBCs versus month of supplementation using different sources and combinations of omega fatty acids.
Figure 5:
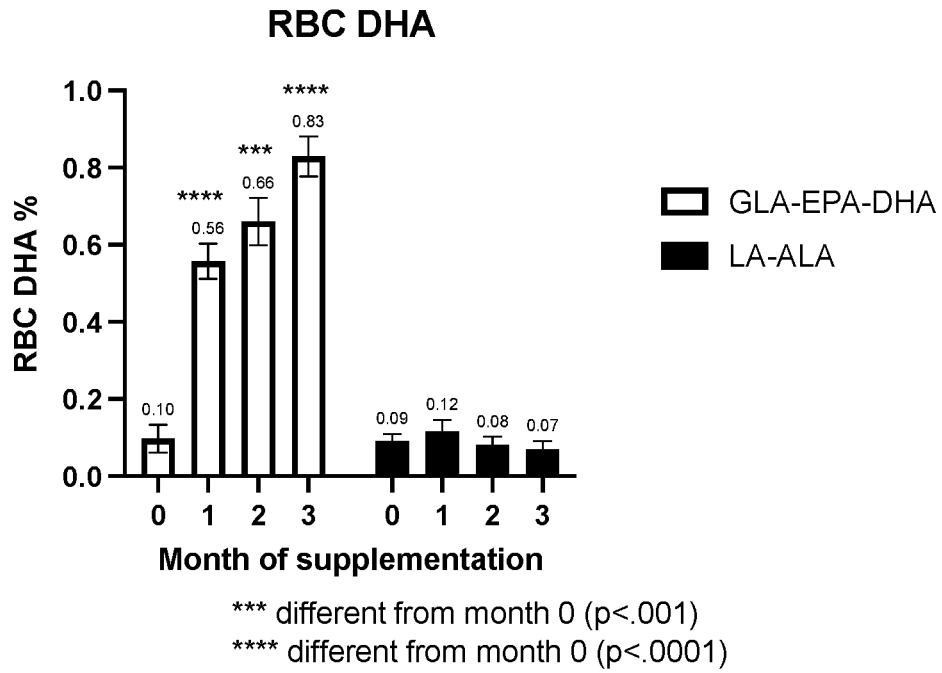
FIG. 5 is a graph showing DHA content of RBCs versus month of supplementation using different sources and combinations of omega fatty acids.

Red blood cell EPA (FIG. 4) and DHA (FIG. 5) were significantly increased in the GLA-EPA-DHA supplemented horses, but not in the LA-ALA oil group. Also, novel eicosanoids generated from long-chain omega-3 PUFAs, termed resolvins and protectins, have anti-inflammatory properties. The most potent anti-inflammatory omega-3 PUFAs are EPA and DHA. Studies in humans have shown that these long-chain omega-3 PUFAs are nine times as potent as ALA. The present study clearly demonstrated that daily intake of EPA+DHA from the GLA-EPA-DHA composition described herein significantly increased RBC membrane EPA+DHA in horses, but that a similar amount of omega-3 in the form of alpha-linolenic acid (ALA) from LA-ALA oil does not. Horses did not appear to be able to efficiently convert ALA into EPA and DHA. Therefore, a dietary source of EPA and DHA like the presently-described GLA-EPA-DHA oil was believed to be needed to affect long-chair omega-3 PUFA cellular membrane composition.

Figure 6:
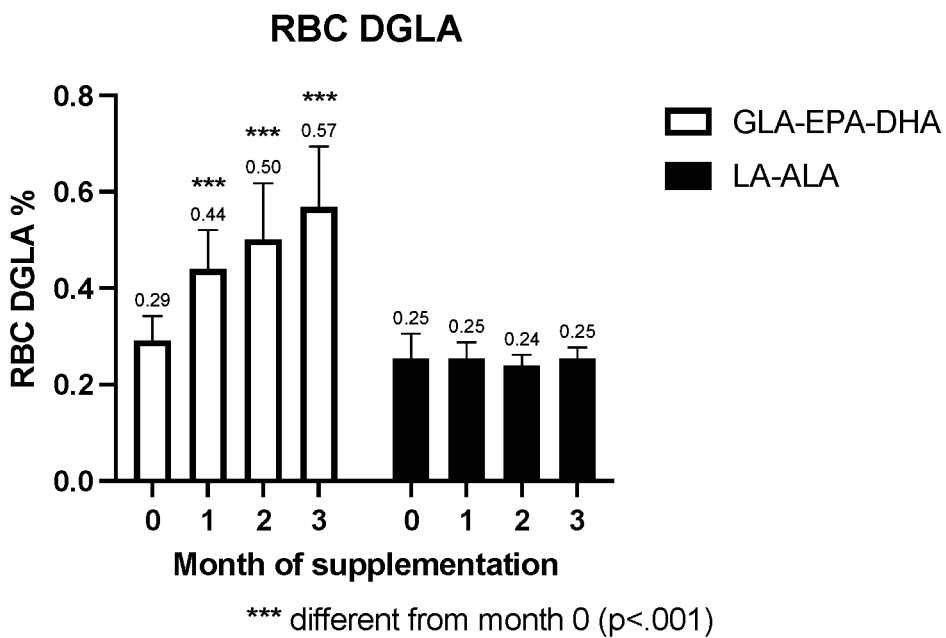
FIG. 6 is a graph showing DGLA content of RBCs versus month of supplementation using different sources and combinations of omega fatty acids.

Red blood cell DGLA (FIG. 6) was significantly increased in the GLA-EPA-DHA supplemented horses, but not in the LA-ALA oil group. Daily intake of 5.4 g GLA from the GLA-DHA-EPA oil blend resulted in a significant increase in both gamma linolenic acid (GLA) (C18:3n6) and dihomo-gamma-linolenic acid (DGLA)(C20:3n6). DGLA is made in the horse's body by the elongation of GLA using an efficient enzyme that does not appear to suffer any form of (dietary) inhibition. DGLA is a precursor of series-1 thromboxane and prostaglandin and a 15-hydroxyl derivative that blocks the transformation of arachidonic acid to leukotrienes. All of these effects are anti-inflammatory.

Figure 7:
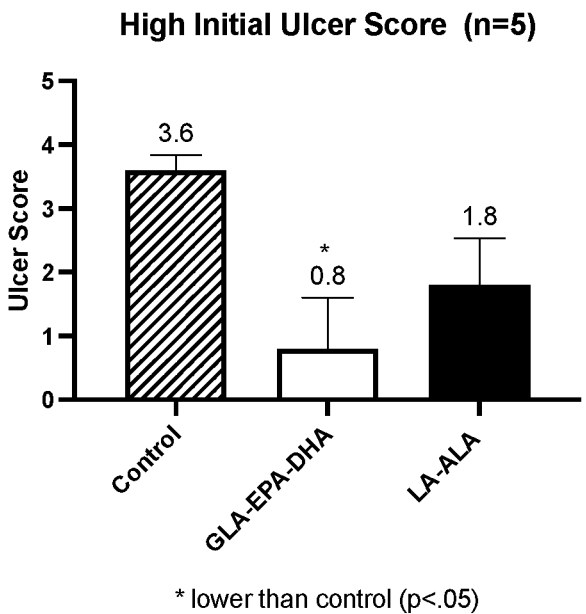
FIG. 7 is a graph showing ulcer score recovery in horses with high (>2) initial ulcer scores after three months of supplementation with different sources and combinations of fatty acids.
Figure 8:
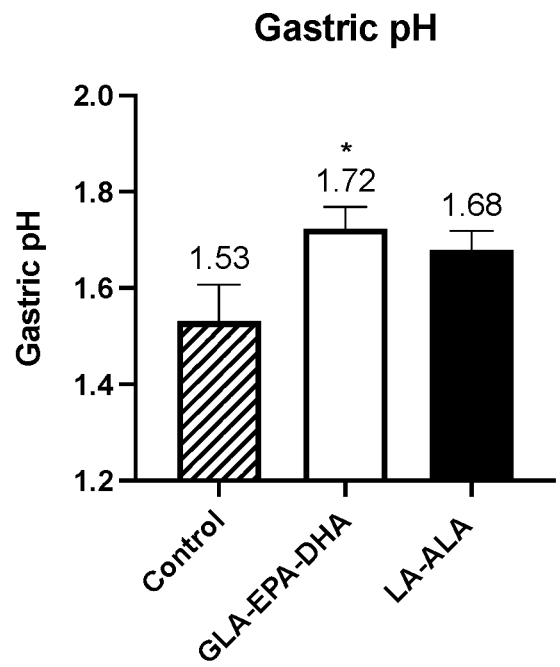
FIG. 8 is a graph showing gastric pH after three months of supplementation with different sources and combinations of fatty acids.
Figure 9:
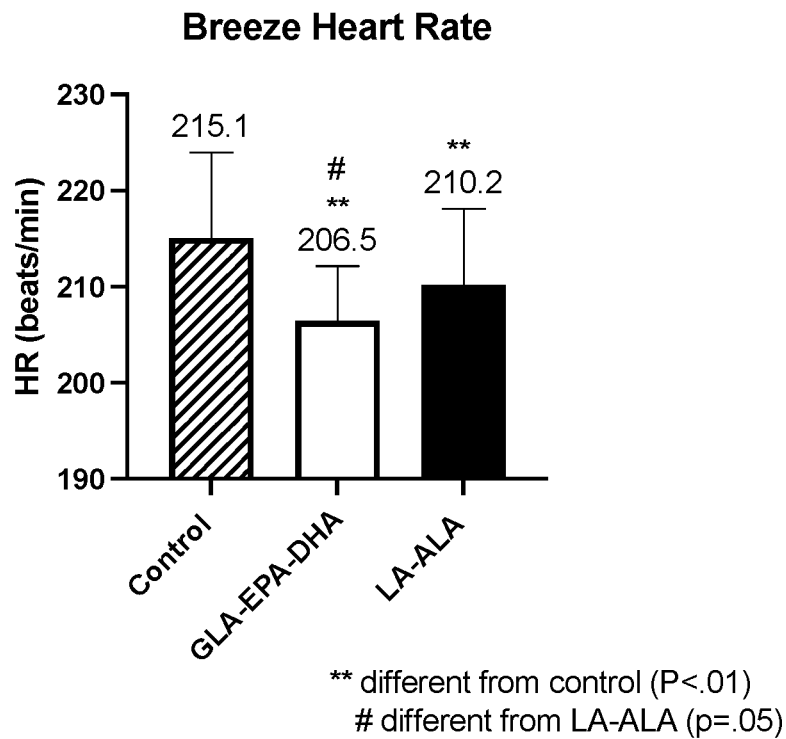
FIG. 9 is a graph showing heart rate during a breeze after three months of supplementation with different sources and combinations of fatty acids.
Figure 10:
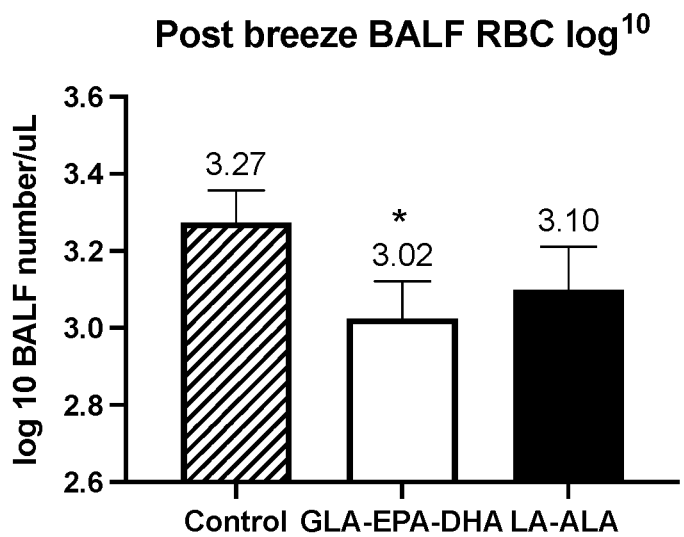
FIG. 10 is a graph showing log 10 RBC number in bronchoalveolar fluid post-breeze after three months of supplementation with different sources and combinations of fatty acids.
Figure 11:
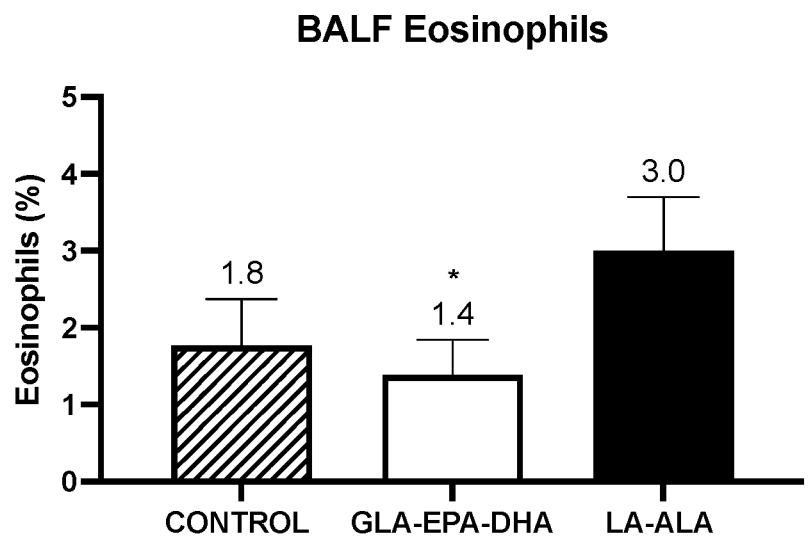
FIG. 11 is a graph showing percent of eosinophils in bronchoalveolar fluid post-breeze after three months of supplementation with different sources and combinations of fatty acids.
Figure 12A:
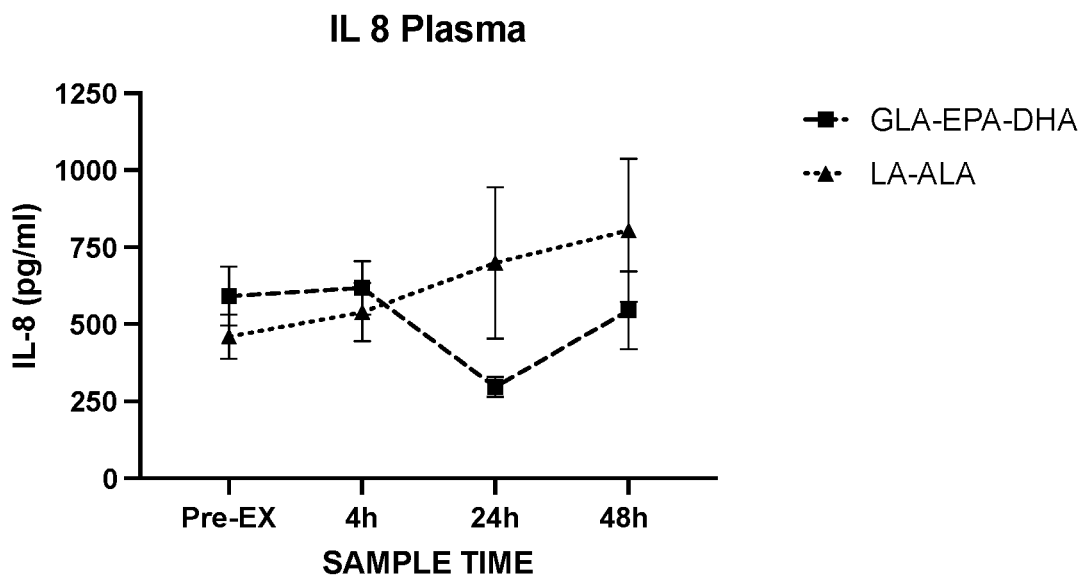
FIGS. 12A-12B are graphs showing plasma cytokine IL-8 (inflammatory) levels (FIG. 12A) and plasma cytokine IL-10 (anti-inflammatory) levels (FIG. 12B) in horses around exercise breezing (exercise stressor) on a dirt racetrack after 3 months of supplementation.
Figure 12B:
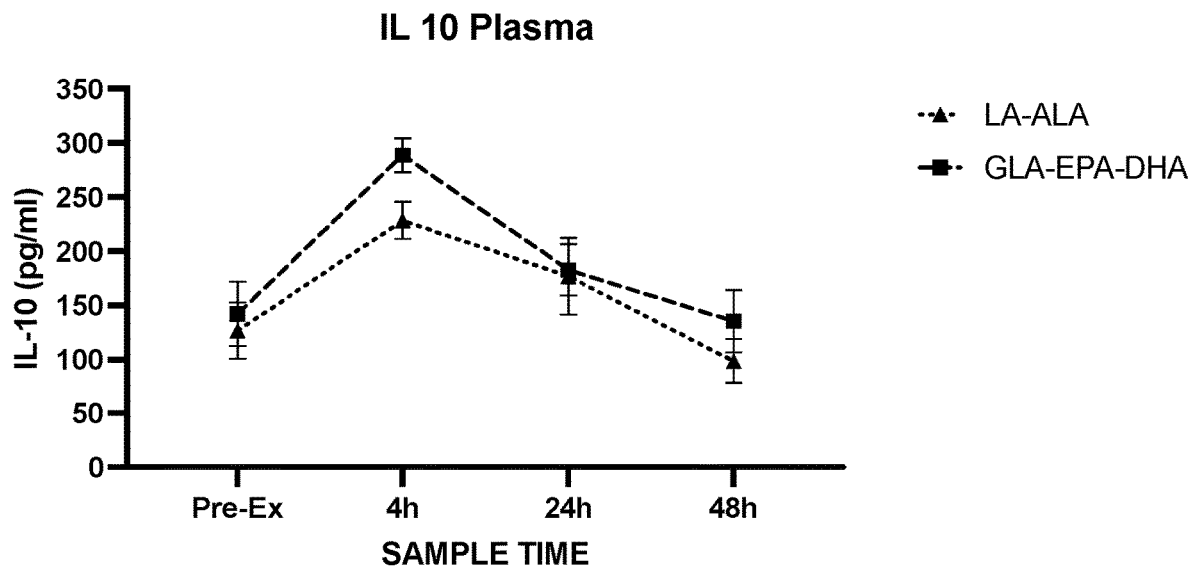

The GLA-EPA-DHA oil blend was further believed to reduce the incidence of gastric ulcers, airway inflammation, and joint inflammation, and can be of benefit in reducing the inflammatory response after exercise. An experiment to examine ulcer score showed positive results for reducing ulcer score (FIG. 7). When horses started supplementation with a high ulcer score (>2), the scores and/or ulcers were significantly reduced after 3 months of supplementation with the GLA-EPA-DHA composition, but not with the LA-ALA oil, compared to the control. This was supported by higher gastric pH when supplemented with the GLA-EPA-DHA oil (FIG. 8). Additionally, GLA-EPA-DHA supplemented horses showed lower heart rates during breezing (FIG. 9), fewer RBCs and eosinophils in bronchoalveolar lavage fluid post-breeze (FIG. 10-11), lower levels of the inflammatory cytokine IL-8 (FIG. 12A), and higher levels of the anti-inflammatory cytokine IL-10 (FIG. 12B) following an exercise stressor. Cytokine levels of IL-8 and IL-10 were altered during exercise recovery when horses were supplemented with GLA-EPA-DHA. IL-8, considered to be an inflammatory cytokine, was decreased at 24 h post-exercise (FIG. 12A). Alternatively, IL-10 is considered to be an anti-inflammatory cytokine and was increased at 4 h post-exercise (FIG. 12B). These results indicate that supplementation with GLA-EPA-DHA can attenuate the inflammatory environment after exercise stress.

Results described herein show positive physiological benefits to supplementing a proprietary blend of GLA, EPA, and DHA. This presently-described blend supplies potent anti-inflammatory long-chain fatty acids directly to the horse.

Example 3—Effect of Polyunsaturated Fatty Acid (PUFA) Supplementation on Red Blood Cell and Plasma Fatty Acid Composition and its Relationship to the Incidence and Severity of Squamous Gastric Ulcers in Exercised Thoroughbreds As described herein above, omega-3 and omega-6 polyunsaturated fatty acids (PUFAs) are essential nutrients for horses. Omega-3 PUFAs include alpha-linolenic acid (ALA, 18:3n3), eicosapentaenoic acid (EPA, 20:5n3), docosapentaenoic acid (DPA, 22:5n3), and docosahexaenoic acid (DHA, 22:6n3). Omega-6 PUFAs include linoleic acid (LA, 18:2n6), gamma-linolenic acid (GLA, 18:3n6), dihomo-gamma-linolenic acid (DGLA, 20:3n6), and arachidonic acid (AA, 20:4n6). PUFAs with 18 or less carbons are considered short chain (SC), while those with 20 or more carbons are long chain (LC). LC-PUFAs serve as precursors for numerous lipid mediators, which are together referred to as eicosanoids and include prostaglandins (PGs), thromboxanes (TXs), and leukotrienes (LTs). Eicosanoids produced from AA tend to be pro-inflammatory, while DGLA, EPA, and DHA give rise to lipid mediators, which are anti-inflammatory and inflammation-resolving. In other species, both omega-3 and omega-6 fatty acids play a role in the prevention and resolution of gastric ulcers.

With that in mind, additional studies were conducted to further evaluate how supplementation with short-chain (e.g., LA, ALA) or longer-chain (e.g., GLA, EPA, DHA) PUFAs affects plasma and red blood cell (RBC) PUFA composition, and how these changes relate to the incidence and severity of squamous gastric ulcers.

Materials and Methods

Horses and feeding management. Thirteen fit Thoroughbred horses (age 4.1±1.9 y, BW 496.0 kg±36.5 kg; mean±SD) housed at the Kentucky Equine Research Performance Center in Ocala, Florida, were used in a 3-period study. During each 88-d period, the horses were fed 4.9±1.4 kg/d (mean±SD) of a textured horse feed fed in 3 meals/d along with 1.0-1.5% BW/d of timothy hay and 60 g loose salt. The horses were stalled for 8 h/d and were turned out in bahiagrass-pasture paddocks for 16 h each night. The proximate analysis and PUFA composition of the feed, hay, and pasture is shown in Table 3 along with the PUFA supplements. The feed, hay, and pasture provided 2.3, 4.9, and 2.9 g/kg (as fed) of ALA and 24.9, 1.5, and 0.8 g/kg (as fed) of LA, respectively. These feedstuffs did not supply measurable quantities of other PUFAs. The study protocol was reviewed and approved by an internal company Institutional Animal Care and Use Committee.

TABLE 3

Proximate analysis and fatty acid composition of feed, hay, pasture, and PUFA supplements.

| | Textured feed (as-fed basis) | Timothy hay (as-fed basis) | Pasture (100% DM basis) | LA-ALA | GLA-EPA-DHA |
|---|---|---|---|---|---|
| Digestible energy (DE, Mcal/kg) | 2.97 | 1.90 | 1.98 | | |
| Crude protein (CP, %) | 12.7 | 10.3 | 17.3 | | |
| Crude fat (%) | 4.9 | 2.3 | 2.8 | 100 | 100 |
| Acid detergent fiber (ADF, %) | 7.9 | 32.5 | 35.9 | | |
| Neutral detergent fiber (NDF, %) | 14.6 | 53.9 | 62.2 | | |
| Starch (%) | 36.2 | 0.7 | 1.8 | | |
| Water-soluble carbohydrate (WSC, %) | 8.4 | 11.3 | 3.9 | | |
| Nonstructural carbohydrate (NSC, %) | 44.6 | 12.0 | 5.7 | | |
| Omega-6 | g/100 g total identified fatty acids | | | | |
| Linoleic acid (LA, C18:2n6) | 48.4 | 16 | 14.6 | 28.9 | 5.6 |
| Gamma-linolenic acid (GLA, C18:3n6) | 0.1 | 0.3 | 0.2 | 0.2 | 12.1 |
| Dihomo-g-linolenic (DGLA, C20:3n6) | 0 | 0 | 0 | 0 | 0.2 |
| Arachidonic acid (AA, C20:4n6) | 0 | 0 | 0 | 0 | 0.8 |
| Omega-3 | | | | | |
| Alpha-linolenic acid (ALA, C18:3n3) | 4.5 | 51.1 | 51.3 | 37 | 1.4 |
| Eicosapentaenoic acid (EPA, C20:5n3) | 0 | 0 | 0 | 0 | 11.1 |
| Docosapentaenoic acid (DPA, C22:5n3) | 0 | 0 | 0 | 0 | 2 |
| Docosahexaenoic acid (DHA, C22:6n3) | 0 | 0 | 0 | 0 | 9.5 |

PUFA supplementation. During period 1, the horses received no PUFA supplementation other than what was contained in the feed, hay, and pasture (CON). Following period 1, horses were split into two groups balanced for age, concentrate intake, bodyweight, and baseline values for exercise speed, gastric pH, and ulcer score. During periods 2 and 3, the horses received either 35 ml/d of a corn oil-flax oil supplement (LA-ALA) or 60 ml/d of a high gamma-linolenic acid (GLA) safflower oil-fish oil supplement (GLA-EPA-DHA) in a switchback design. Seven horses received GLA-EPA-DHA first while the other six horses received LA-ALA first before switching to the other treatment. During a 10-day washout period between periods 2 and 3, the horses did not receive PUFA supplementation. Each supplement was divided into two daily feedings. The LA-ALA supplement provided 8.0 g LA and 10.2 g ALA per day. The GLA-EPA-DHA supplement provided 2.5 g LA, 5.4 g GLA, 0.3 g AA, 4.4 g EPA, 0.8 g DPA, and 3.8 g DHA per day. Each supplement provided a similar amount of total omega-6 (8.0 g LA-ALA vs 8.2 g GLA-EPA-DHA) and omega-3 (10.2 g LA-ALA vs 9.6 g GLA-EPA-DHA) per day.

Exercise schedule. During the first 77 days of each period, horses were exercised 3 times per week on a 1,600-m dirt racetrack. Across all periods, each session averaged 3,640±590 m and lasted 12.3±0.5 min. During each session, horses walked 275±67 m (1-3 m/s), trotted 1,115±285 m (3-5 m/s), cantered 1,520±470 m (5-10 m/s), and galloped 730±325 (>10 m/s). The horses cantered or galloped 4.0±1.1 min of each session with heart rates ≥154 bpm. The horses also walked 30 min/session 3 days per week on a 20-m diameter mechanical walker.

On day 81 of each period, the horses performed a 4,600-m standardized exercise test (SET) on the racetrack consisting of 1,800-m trot (4.5±0.4 m/s), 1,200-m canter (8.2±1.0 m/s), 600-m fast gallop (15.3±0.6 m/s), and 1,000-m canter (8.7±1.7 m/s). Horses did not perform any forced exercise for 2 weeks following the SET.

Gastroscopy and gastric fluid collection. Five days after the SET (d 86), the gastric mucosa of the horses was examined using a flexible 3-m videoendoscope (Olympus OSF-V60) while sedated with detomidine (0.01 mg/kg) (Dormosedan, Zoetis). Prior to gastroscopy, feed and hay were withheld 15-18 h and water withheld 2-3 h. The severity of squamous gastric ulceration was scored on a scale of 0-4 in accordance with an equine gastric lesion scoring system by a researcher who was unaware of the diet each horse was being fed. A score of 0 was considered free of ulceration, scores of 1-2 were considered mild to moderate ulceration, and scores of 3-4 were considered severe ulceration. Gastroscopic evaluations followed the collection of 200-300 mL gastric fluid through the biopsy port of the endoscope for pH analysis. Gastric fluid samples were immediately evaluated for pH after collection using a benchtop pH meter (Oakton pH 700 Benchtop Meter, model 35419-12).

Blood collection and fatty acid analysis. Blood samples were collected monthly during each period to evaluate changes in plasma and RBC fatty acid composition. The final sample from each period was collected two days after the gastroscopy (d 88). Prior to morning feeding (0600-0700 h), samples were collected via venipuncture of the jugular vein directly into $K_2$EDTA vacutainers. Vacutainers were placed at 4° C. until they could be centrifuged at 1,500×g for 10 minutes as soon as possible (≤10 minutes). After centrifugation, plasma was collected and placed into separate aliquots. The buffy coat was carefully discarded via aspiration to access RBCs. RBCs were then collected and placed into separate aliquots. Samples were either immediately sent overnight at ambient temperature to a commercial laboratory (OmegaQuant Analytics, Sioux Falls, SD) where they were frozen at −80° C. until analysis, or they were frozen at −80° C. after collection and sent overnight on dry ice to the same laboratory. Plasma and RBC samples were processed and analyzed for fatty acid composition using gas chromatography with flame ionization. A total of 24 fatty acids were identified for every sample.

Statistical Analysis. Data was analyzed using Prism (GraphPad) statistical software. Values are mean±SD unless specified otherwise and levels of significance were set at α≤0.05. Significant differences in RBC and plasma fatty acid levels between treatments were determined using a one-way ANOVA for repeated measures followed by a Tukey post-hoc test. Significant differences in RBC fatty acid composition between ulcer groups were determined using a two-tailed, unpaired T test. Odds ratios were used to quantify the relationship between PUFA supplementation and severity of squamous ulcer score (MedCalc3).

Results

Figure 13A:
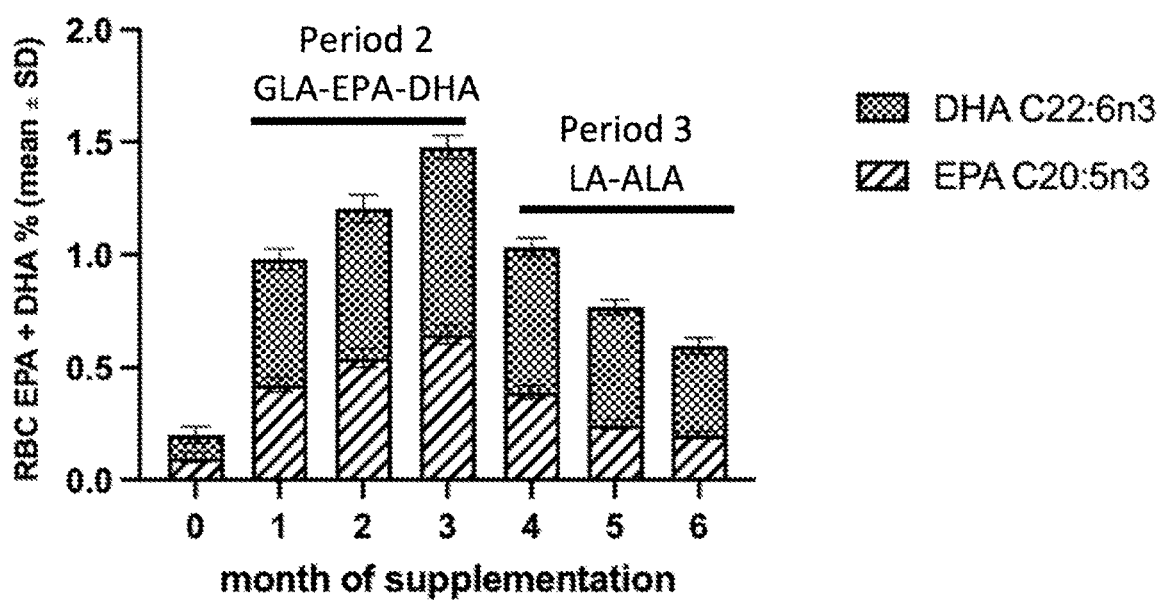
FIGS. 13A-13B are graphs showing RBC EPA and DHA in horses that received GLA-EPA-DHA before LA-ALA (FIG. 13A) (n=7) and in horses that received GLA-EPA-DHA after LA-ALA (FIG. 13B) (n=6) during later periods.
Figure 13B:
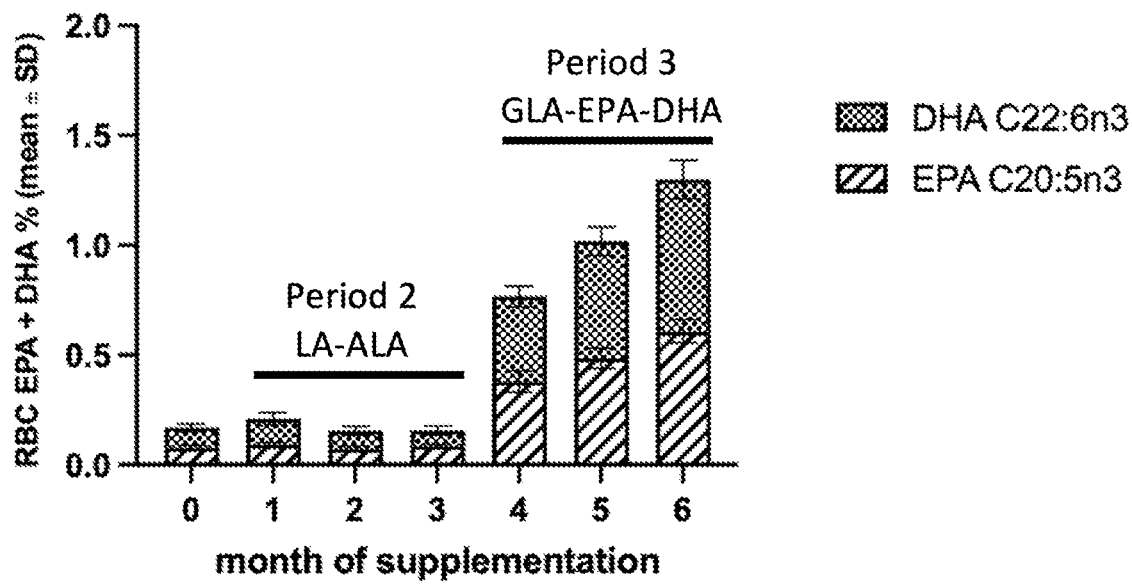

Supplementation with GLA-EPA-DHA resulted in a decrease in RBC and plasma LA and ALA (p<0.05) and an increase in RBC and plasma GLA, DGLA, EPA, and DHA (p<0.05) compared to CON or LA-ALA-supplemented horses. RBC AA was also higher in GLA-EPA-DHA-supplemented horses (p<0.05). RBC GLA, DGLA, EPA, and DHA were elevated in LA-ALA horses compared to CON horses during period 3 due to a carryover effect following GLA-EPA-DHA supplementation in period 2 (Table 4 and FIG. 13).

All observations (n=39) were grouped to compare RBC fatty acid composition to ulcer score. The PUFA composition of all horses with no or mild to moderate ulcers (grade 0-2; n=30) is shown in Table 6 compared to horses with severe (grade 3-4) ulcer scores (n=9). RBC GLA, DGLA, EPA and AA were all higher in horses with grade 0-2 ulcers compared to horses with severe ulcers (grade 3-4) (p<0.05). Gastric fluid pH was also higher (1.69±0.20) in the horses with no or mild to moderate ulcers compared to the horses with severe ulcers (1.51±0.22) (p<0.05).

TABLE 4

RBC and plasma PUFA composition (d 88) when horses were unsupplemented (CON) or fed LA-ALA or GLA-EPA-DHA supplements (g/100 g total identified fatty acids).

| | CON | LA-ALA | | | | GLA-EPA-DHA | | |
|---|---|---|---|---|---|---|---|---|
| | Period 1 (n = 13) | Period 2 (n = 6) | Period 3 (n = 7) | TOTAL (n = 13) | | Period 2 (n = 7) | period 3 (n = 6) | TOTAL (n = 13) |
| RBC fatty acids | | | | | | | | |
| LA C18:2n6 | 39.64 ± 0.93$^a$ | 39.93 ± 0.97 | 38.33 ± 0.82 | 39.07 ± 1.19$^{a*}$ | | 37.98 ± 1.13 | 37.12 ± 0.70 | 37.59 ± 1.02$^b$ |
| ALA C18:3n3 | 1.27 ± 0.33$^a$ | 1.34 ± 0.26 | 1.09 ± 0.18 | 1.21 ± 0.25$^a$ | | 1.04 ± 0.24 | 1.10 ± 0.24 | 1.07 ± 0.23$^b$ |
| GLA C18:3n6 | 0.10 ± 0.04$^a$ | 0.12 ± 0.01 | 0.17 ± 0.03 | 0.15 ± 0.03$^{b*}$ | | 0.38 ± 0.04 | 0.37 ± 0.09 | 0.37 ± 0.07$^c$ |
| DGLA C20:3n6 | 0.27 ± 0.05$^a$ | 0.25 ± 0.02 | 0.38 ± 0.05 | 0.32 ± 0.07$^{a*}$ | | 0.57 ± 0.13 | 0.51 ± 0.08 | 0.54 ± 0.11$^b$ |
| AA C20:4n6 | 1.48 ± 0.26$^a$ | 1.31 ± 0.21 | 1.39 ± 0.24 | 1.36 ± 0.22$^b$ | | 1.68 ± 0.23 | 1.53 ± 0.22 | 1.61 ± 0.23$^c$ |
| EPA C20:5n3 | 0.09 ± 0.05$^a$ | 0.09 ± 0.02 | 0.2 ± 0.04 | 0.15 ± 0.06$^{b*}$ | | 0.65 ± 0.11 | 0.61 ± 0.13 | 0.63 ± 0.12$^c$ |
| DHA C22:6n3 | 0.09 ± 0.07$^a$ | 0.12 ± 0.07 | 0.39 ± 0.10 | 0.27 ± 0.17$^{b*}$ | | 0.83 ± 0.14 | 0.69 ± 0.21 | 0.77 ± 0.18$^c$ |
| (EPA+DHA) | 0.18 ± 0.11$^a$ | 0.16 ± 0.07 | 0.60 ± 0.11 | 0.39 ± 0.24$^{b*}$ | | 1.47 ± 0.20 | 1.30 ± 0.34 | 1.39 ± 0.28$^c$ |
| (DGLA + AA) | 1.76 ± 0.30$^a$ | 1.57 ± 0.23 | 1.77 ± 0.26 | 1.67 ± 0.26$^a$ | | 2.25 ± 0.32 | 2.04 ± 0.29 | 2.15 ± 0.31$^b$ |
| (DGLA + AA + EPA + DHA) | 1.94 ± 0.37$^a$ | 1.72 ± 0.27 | 2.36 ± 0.24 | 2.07 ± 0.41$^{a*}$ | | 3.72 ± 0.47 | 3.34 ± 0.59 | 3.55 ± 0.54$^b$ |
| Plasma fatty Acids | | | | | | | | |
| LA C18:2n6 | 54.04 ± 1.46$^a$ | 55.12 ± 1.24 | 54.80 ± 0.45 | 54.94 ± 0.88$^a$ | | 53.52 ± 1.19 | 52.34 ± 1.01 | 52.98 ± 1.23$^b$ |
| ALA C18:3n3 | 2.87 ± 1.04$^a$ | 2.63 ± 0.38 | 2.10 ± 0.23 | 2.34 ± 0.40$^a$ | | 1.81 ± 0.46 | 1.89 ± 0.48 | 1.85 ± 45$^b$ |
| GLA C18:3n6 | 0.08 ± 0.04$^a$ | 0.13 ± 0.01 | 0.17 ± 0.06 | 0.15 ± 0.05$^{b*}$ | | 0.83 ± 0.12 | 0.77 ± 0.22 | 0.80 ± 0.16$^c$ |
| DGLA C20:3n6 | 0.33 ± 0.08$^a$ | 0.30 ± 0.03 | 0.51 ± 0.05 | 0.41 ± 0.12$^{a*}$ | | 0.69 ± 0.15 | 0.81 ± 0.09 | 0.75 ± 0.13$^b$ |
| AA C20:4n6 | 1.39 ± 0.21$^a$ | 1.14 ± 0.14 | 1.25 ± 0.13 | 1.20 ± 0.14$^b$ | | 1.45 ± 0.19 | 1.47 ± 0.14 | 1.46 ± 0.16$^a$ |
| EPA C20:5n3 | 0.09 ± 0.04$^a$ | 0.07 ± 0.02 | 0.18 ± 0.06 | 0.13 ± 0.07$^a$ | | 0.57 ± 0.09 | 0.65 ± 0.06 | 0.61 ± 0.08$^b$ |
| DHA C22:6n3 | 0.07 ± 0.05$^a$ | 0.12 ± 0.06 | 0.35 ± 0.12 | 0.24 ± 0.15$^{b*}$ | | 0.86 ± 0.12 | 0.85 ± 0.12 | 0.85 ± 0.12$^c$ |
| EPA + DHA | 0.16 ± 0.06$^a$ | 0.18 ± 0.08 | 0.53 ± 0.14 | 0.36 ± 0.21$^{b*}$ | | 1.43 ± 0.17 | 1.5 ± 0.17 | 1.46 ± 0.17$^c$ |
| DGLA + AA | 1.73 ± 0.26$^a$ | 1.44 ± 0.15 | 1.76 ± 0.13 | 1.61 ± 0.21$^a$ | | 2.14 ± 0.27 | 2.28 ± 0.12 | 2.20 ± 0.22$^b$ |
| (DGLA + AA + EPA + DHA) | 1.89 ± 0.29$^a$ | 1.62 ± 0.18 | 2.29 ± 0.10 | 1.98 ± 0.37$^{a*}$ | | 3.57 ± 0.36 | 3.77 ± 0.26 | 3.66 ± 0.32$^b$ |

Unlike superscripts in a row are significantly different. *Period effect seen in LA-ALA due to carryover effect of GLA-EPA-DHA supplementation in period 2

Gastric ulcers. The overall prevalence of gastric ulcers (grade 1-4) was 54%, 46%, and 31% in the CON, LA-ALA, and GLA-EPA-DHA groups, respectively (Table 5). Five of the 13 horses (38%) had severe ulcers (grade 3-4) at the end of the CON period. None of the other 8 horses developed severe ulcers during the rest of the study. When supplemented with GLA-EPA-DHA, significantly fewer horses (1 of 13, 8%) had a severe ulcer (OR 0.13; 95% CI 0.013-1.36; p<0.05; z score 1.70). LA-ALA supplemented horses had a 23% (3 of 13) incidence of severe ulceration, which was not different from CON or GLA-EPA-DHA (p>0.05).

TABLE 5

Number of horses with each ulcer score per treatment.

| | ULCER SCORE | | | | | |
|---|---|---|---|---|---|---|
| | 0 | | 1-2 | | 3-4 | |
| TREATMENT | number | % | number | % | number | % |
| CON | 6 | 46% | 2 | 15% | 5 | 38% |
| LA-ALA | 7 | 54% | 3 | 23% | 3 | 23% |
| GLA-EPA-DHA | 9 | 69% | 3 | 23% | 1 | 8% |

TABLE 6

RBC PUFA composition of horses with either grade 0-2 ulcers (n = 30) or grade 3-4 ulcers (n = 9).

| | Ulcer Score | | |
|---|---|---|---|
| | 0-2 | 3-4 | |
| RBC Fatty | n = 30 | n = 9 | |
| acid | g/100 g total fatty acids | | p value |
| ALA | 1.23 ± 0.26 | 1.03 ± 0.32 | 0.06 |
| LA | 38.58 ± 1.36 | 39.4 ± 1.18 | 0.11 |
| GLA | 0.23 ± 0.14 | 0.13 ± 0.05 | <0.05 |
| DGLA | 0.40 ± 0.15 | 0.30 ± 0.09 | <0.05 |
| EPA | 0.33 ± 0.27 | 0.14 ± 0.13 | <0.05 |
| DHA | 0.42 ± 0.34 | 0.21 ± 0.21 | 0.09 |
| AA | 1.54 ± 0.24 | 1.29 ± 0.22 | <0.01 |
| DGLA + AA | 1.94 ± 0.35 | 1.59 ± 0.24 | <0.01 |
| EPA + DHA | 0.75 ± 0.61 | 0.35 ± 0.32 | 0.06 |
| GLA-EPA-DHA | 2.69 ± 0.88 | 1.94 ± 0.40 | <0.05 |

Figure 14:
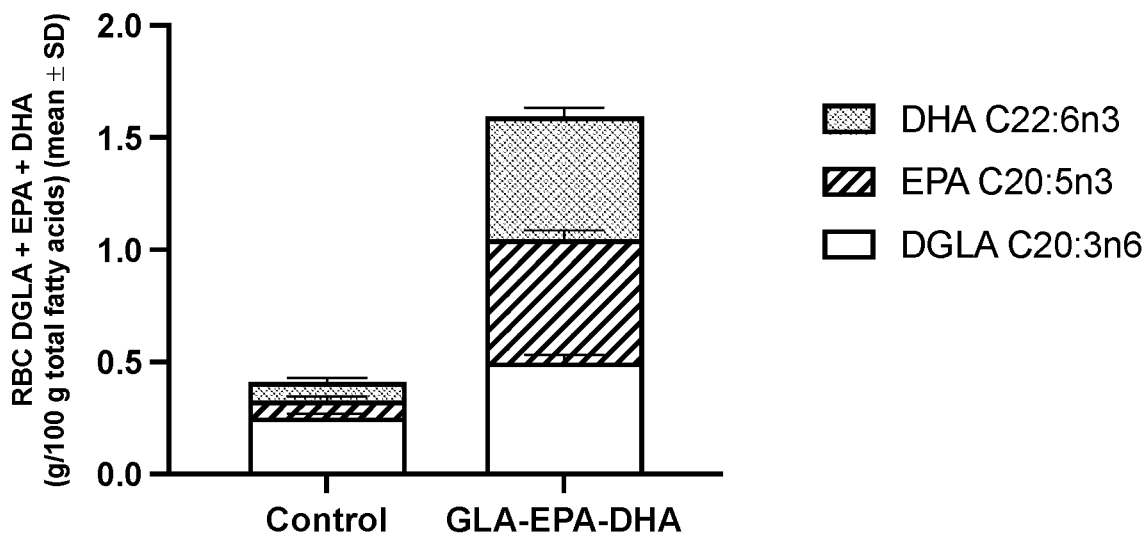
FIG. 14 is a graph showing RBC DGLA, EPA, and DHA levels (g/100 g of total fatty acids) in 5 horses with severe ulcers (grade 3-4) before (control) and in these same horses after 3 months of supplementation with GLA-EPA-DHA.

The five horses that had severe ulceration initially (period 1, CON) were subgrouped to evaluate supplementation. In these horses, supplementation with GLA-EPA-DHA resulted in higher RBC DGLA, EPA, and DHA (p<0.05) (FIG. 14), and four of the five had no ulcers (grade 0) after 3 months of GLA-EPA-DHA supplementation, regardless of period. Two of these horses redeveloped ulcers when subsequently placed on the LA-ALA supplement and one horse was resistant to any changes.

Discussion

There are two families of essential fatty acids (EFAs), omega-6 polyunsaturated fatty acids (PUFAs) derived from linolenic acid (LA), and the omega-3 PUFAs derived from alpha-linolenic acid (ALA). Essential fatty acids cannot be synthesized by the body, but the body can desaturate and elongate EFAs provided by the diet. These pathways are responsible for not only producing PUFAs found in the membranes for virtually every cell in the body, but also generating prostaglandins (PGs) and other eicosanoids involved in the pathophysiology, prevention, and treatment of gastric ulcers. Generally, these pathways work in balance, producing pro-inflammatory and anti-inflammatory compounds. Linolenic acid, the parent of the omega-6 pathway, is desaturated to form gamma-linolenic acid (GLA), which in turn is elongated to form dihomo-GLA (DGLA), the precursor of PG1 series. DGLA can also be desaturated by delta-5-desaturase to arachidonic acid (AA), the precursor of PG2 series. Alpha-linolenic acid, the parent of the omega-3 pathway, is desaturated and elongated by the same set of enzymes to give rise to eicosapentaenoic acid (EPA), the precursor of PG3 series, and further to docosahexaenoic acid (DHA), a precursor to resolvins and protectins involved in inflammation.

These pathways compete for the same enzymes in their elongation steps. Although the ideal omega-6:omega-3 ratio has not been established for horses, it is clear that the current feeding practices of performance horses has drastically skewed the ratio from a natural forage-based diet. An all-forage diet would provide a 0.3:1 (omega-6:omega-3) ratio. In this study, the basal diet provided about 140 g/d LA and 62 g/d ALA for a ratio of 2.2:1. When horses were supplemented in the current study, treatments were matched to provide similar omega-6:omega-3 ratios (0.8:1) so as to only evaluate the type of FA (SC vs LC) fed rather than an impact on the ratio. Studies in other species have ratios from 5.3-665:1, and studies in horses have ratios of 0.8-7.5:1, if they are listed at all.

Traditionally, PUFAs in equine diets have been provided as SC-PUFAs from vegetable oils and forage. The predominant form of omega-6 SC-PUFA (LA) comes from vegetable oils, such as corn and soy oil, while the major SC-PUFA omega-3 (ALA) is supplied from forage or vegetable oils such as flaxseed oil. In the present study, horses fed supplemental LA and ALA from corn oil and flax oil did not increase LC-PUFAs in plasma or RBC. Horses fed GLA-EPA-DHA had reduced RBC and plasma LA and ALA, and increased EPA, DHA, and AA. This agrees with previous studies in which horses fed fish oil had greater (p<0.05) proportions of EPA, DHA, and AA in plasma and RBC, and plasma LA and ALA were less (p<0.05) compared with those supplemented with flax oil. Additionally, horses not supplemented directly with EPA and DHA did not increase their plasma or RBC levels. This reflects an inability to adequately elongate dietary SC-PUFAs like ALA and LA to LC-PUFAs like DGLA, EPA, and DHAs and highlights the benefits of supplementing LC-PUFAs directly. This allows the horse to avoid minimally effective and competitive elongation steps. Interestingly, GLA is considered a SC-PUFA, but has been shown both here and in other unpublished research from the present inventors research to be efficiently elongated to the LC-PUFA DGLA by the horse. It is possible that concurrently supplying LC-PUFAs EPA and DHA allow for GLA to be efficiently converted to DGLA and AA and their respective PGs. Some research has shown a reduction in AA when fed fish oil, but the present study has demonstrated an increase in DGLA and AA that is likely attributable to supplying GLA. The GLA-EPA-DHA treatment with GLA increased RBC levels of AA compared to CON, and the LA-ALA treatment showed a decrease in RBC AA. Although plasma levels of AA were not different between GLA-EPA-DHA and CON, LA-ALA had significantly lower AA levels than CON.

RBCs are longer-lived than platelets and lipoproteins, so their fatty acid composition is more stable and reflective of chronic omega-3 status. Previous studies in horses demonstrated augmented levels of omega-3 PUFAs in plasma, RBCs, leukocytes, synovial fluid, and skeletal muscle following EPA and DHA supplementation. Data from mice demonstrated that the gastrointestinal tissues are highly responsive to dietary LC-PUFA supplementation and that the sum of EPA+DHA in RBCs, expressed as a percentage of total fatty acids (the omega-3 index), can serve as a valid biomarker for assessing dietary EPA+DHA incorporation into gastrointestinal tissues. Although gastrointestinal tissue was not measured in this study, levels of fatty acids in RBCs, including EPA+DHA, were altered by dietary supplementation and may be reflective of changes to local gastric tissue.

Prostaglandins produced from fatty acids can influence acid, mucus, and bicarbonate secretion in addition to accelerated healing of ulcers. AA from the omega-6 pathway produces PGE2 while PGE1 and PGE3 are produced from DGLA and EPA through the omega-6 and omega-3 pathway, respectively. NSAIDS block the production of all three PGEs through disruption of the cyclooxygenase (COX) pathway and have been implicated in increased risk for gastric ulcers. When it comes to gastric protection, PGE2 from AA is thought to play an important role during stress. Studies have shown that PGE2 deficiency can increase mucosa susceptibility to ulceration and that increased erosion has been seen with decreased levels of AA, largely due to a decrease in PGE2 production. When supplied with LA as a precursor to AA, the horse has been able to increase gastric PGE2 production and lower gastric acid output. However, GLA supplementation was preferred to LA in rats subjected to aspirin-induced gastric hemorrhage. GLA supplementation produced higher levels of AA and no gastric hemorrhage compared to hemorrhage in 3 of 8 rats on the LA diet. It was believed GLA was able to bypass depressed levels of delta-6-desaturation in the LA group and protect gastric mucosa through improved synthesis of AA and PGEs. Similarly, supplementation of LA in the present study's LA-ALA treatment did not increase AA levels but reduced levels. Although gastric PGE2 was not measured in this study, it may be inferred that an increase in AA in the GLA-EPA-DHA treatment likely resulted in an increase in PGE2 and could be attributed to the reduced pH and ulcer prevalence and severity in the GLA-EPA-DHA group. Horses with severe ulceration (grade 3-4) had lower RBC AA levels as well as lower GLA, DGLA, and EPA compared to those with no or mild to moderate ulcers (grade 0-2).

Other studies in mice have shown chronic or acute administration of EPA or DHA from fish oil to be effective in reducing or protecting gastric injury when subjected to ethanol-induced hemorrhagic gastritis or mechanical, chemical, and thermic stress. DHA was also found to be protective against indomethacin-induced gastric damage akin to omeprazole. This gastroprotective effect was found to not be through mediation of PGE2, but by a decrease in gastric B4 leukotriene levels. A collection of data indicates that fish oil is able to protect gastric mucosa by both offensive (inhibiting acid secretion) and defensive (enhancing mucus secretion, activity of antioxidant enzymes) factors. Overall, the use of a LC-PUFA product with GLA, EPA, and DHA may allow for utilization of multiple approaches to gastric protection and ulcer prevention. GLA-EPA-DHA supplementation used in this study was positively associated with prevention or resolution of severe squamous gastric ulceration in exercising Thoroughbreds.

Most research has utilized an induced-ulceration model for study, and a variety of models are used that can complicate the interpretation of results. However, this study was able to evaluate naturally occurring ulcers from performance horses subjected to typical stress exercise as recommended by the Equine Gastric Ulcer Council. The difference between the generation of naturally occurring ulcers and those induced by mechanical, chemical, or other stress factors may be significant in characterizing the mechanisms behind preventing and improving ulceration of gastric mucosa. Mucosal damage depends on the nature of the injury and has been shown to be significantly affected by fatty acid composition. Although ulcers were naturally occurring in this study, the prevalence (31-54%, grade 1-4) was lower compared to surveys of other racehorses (52-92%, 66%, 72%, 82%, 93%). This study was considered less intense than race training (64% of training distance and 77% of time in HR >154 bpm) and horses were housed outside at night compared to stabled approximately 23 hr/d. This moderation in horse management may have also played a role in the ulcer prevalence and results observed in this study.

In summary, the above-described study has shown that horses lack the ability to adequately elongate SC-PUFAs LA and ALA to LC-PUFAs, like DGLA, EPA, and DHAs, which agrees with findings of other researchers. This subsequently limits their ability to produce valuable eicosanoids like PGE2 that have been implicated in the resolution of gastric ulceration. The presence of squamous gastric disease in horses, especially those involved in high-performance competition, ranks high among health concerns of owners and trainers. In many instances, medications such as omeprazole or sucralfate are prescribed to heal ulcers, and specific nutritional strategies are put into place to prevent recurrence. The above results indicate that supplementation with GLA-EPA-DHA oil blends, is a viable way to prevent or resolve severe squamous gastric ulceration in equine athletes during training.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Sykes B, Hewetson M, Hepburn R, Luthersson N, Tamzali, Y. European College of Equine Internal Medicine Consensus Statement—Equine Gastric Ulcer Syndrome in Adult Horses. J Vet Intern Med 2015; 29:1288-1299. https://doi.org/10.1111/jvim.13578
2. Harris W S, Schmitt T L. Unexpected similarity in RBC DHA and AA levels between bottlenose dolphins and humans. Prostaglandins Leukot Essent Fatty Acids 2014; 90(2):55-59. https://doi.org/10.1016/j.plefa.2013.12.005
3. MedCalc Software Ltd. Odds ratio calculator. MedCalc. Accessed May 7, 2022.
4. Wilson D E. Prostaglandins in peptic ulcer disease. Their postulated role in the pathogenesis and treatment. Postgrad Med. 1987; 81(4):309-16. PMID:3547381.
5. Olafsson S O, Hallgrimsson J, Gudbjarnason S. Dietary cod liver oil decreases arachidonic acid in rat gastric mucosa and increases stress-induced gastric erosions. Lipids 2000; 35(6):601-605. https://doi.org/10.1007/s11745-000-0562-6
6. Khol-Parisini A, van den Hoven R, Leinker S, Hulan H W, Zentek J. Effects of feeding sunflower oil or seal blubber oil to horses with recurrent airway obstruction. Can J Vet Res. 2007; 71, 59-65.
7. King S S, Abughazaleh A A, Webel S K, Jones K L. Circulating fatty acid profiles in response to three levels of dietary omega-3 fatty acid supplementation in horses. J Anim Sci. 2008; 86, 1114-1123.
8. Vineyard K R, Warren L K, Kivipelto J. Effect of dietary omega-3 fatty acid source on plasma and red blood cell membrane composition and immune function in yearling horses. J Anim Sci. 2010; 88:248-257. https://doi.org/10.2527/jas.2009-2253
9. Hess T M, Rexford J K, Hansen D K, et al. Effects of two different dietary sources of long chain omega-3, highly unsaturated fatty acids on incorporation into the plasma, red blood cell, and skeletal muscle in horses. J Anim Sci. 2012; 90, 3023-3031.
10. Ross-Jones T N, Hess T, Rexford J K, Ahrens N, Engle T E, Hansen D K. Effects of omega-3 long chain fatty acid supplementation on equine synovial fluid fatty acid composition and prostaglandin E2. J Equine Vet Sci. 2014; 34:779-783.
11. Hess T, Braun, S, Herkelman, K. The effects of various levels of docosahexaenoic acid on inflammatory markers in conditioned horses during lactate threshold tests. J Equine Vet Sci. 2019; 72:64-71.
12. Harris W S, Varvel S A, Pottala J V, Warnick G R, McConnell J P. Comparative effects of an acute dose of fish oil on omega-3 fatty acid levels in red blood cells versus plasma: implications for clinical utility. J Clin Lipidol. 2013; 7(5)433-440.
13. Nogradi N, Couetil L L, Messick J, Stochelski M A, Burgess J R. Omega-3 fatty acid supplementation provides an additional benefit to a low-dust diet in the management of horses with chronic lower airway inflammatory disease. J Vet Intern Med. 2015; 29, 299-306.
14. Ross-Jones T N, McIlwraith C W, Kisiday J D, Hess T M, Hansen D K, Black J. Influence of an n-3 long chain polyunsaturated fatty acid-enriched diet on experimentally induced synovitis in horses. J Anim Physiol Anim Nutr. 2016; 100:565-577.
15. Harris W S, C Von Schacky. The omega-3 index: a new risk factor for death from coronary heart disease? Preventive Medicine 2004; 39:212-220.
16. Gurzell E A, Wiesinger J, Morkam C, Hemmrich S, Harris W, Fenton J. Is the omega-3 index a valid marker of intestinal membrane phospholipid EPA+DHA content? Prostaglandins Leukot Essent Fatty Acids. 2014; 91(3): 87-96.
17. Whittle B J R, Lopez-Belmonte J, Moncada S. Regulation of gastric mucosal integrity by endogenous nitric oxide: interaction with prostanoids and sensory neuropeptides in the rat. Br J Pharmacol. 1990; 99:607-611.
18. Kobayashi K, Arakawa T. Arachidonic acid cascade and gastric mucosal injury, protection, and healing: topics of this decade. J Clin Gastroenterol. 1995; 21:S12-S17.

19. Cargile J L, Burrow J A, Kim I, Cohen N D, Merritt A M. Effect of dietary corn oil supplementation on equine gastric fluid acid, sodium, and prostaglandin E2 content before and during pentagastrin infusion. J Vet Intern Med. 2005; 18(4):545-549.
20. Huang Y S, Drummond R, Horrobin D F. Protective effect of gamma-linolenic acid on aspirin-induced gastric hemorrhage in rats. Digestion 1987; 36:36-41.
21. Hunter B, McDonald G S, Gibney M J. The effects of acute and chronic administration of n-6 and n-3 polyunsaturated fatty acids on ethanol-induced gastric haemorrhage in rats. Br J Nutr. 1992; 67:501-507.
22. Leung F W. Prostaglandins mediate fish oil protection against ethanol-induced gastric mucosal injury in rats. Dig Dis Sci. 1994; 39:893.
23. Al-Harbi M M, Islam M W, Al-Shabanah O A, Algharably N M. Effect of acute administration of fish oil (omega-3 marine triglyceride) on gastric ulceration and secretion induced by various ulcerogenic and necrotizing agents in rats. Food Chem Toxicol. 1995; 33:553-558.
24. Pineda-Peña E A, Jiménez-Andrade J M, Castañeda-Hernández G, Chávez-Piña A E. Docosahexaenoic acid, an omega-3 polyunsaturated acid protects against indomethacin-induced gastric injury. Eur J Pharmacol. 2012; 697:139-143.
25. Bhattacharya A, Ghosal S, Bhattacharya S K. Effect of fish oil on offensive and defensive factors in gastric ulceration in rats. Prostaglandins Leukot Essent Fatty Acids. 2006; 74:109-116.
26. Murray M J, Grodinsky C, Anderson C W, Radue P F, Schmidt G R. Gastric ulcers in horses: a comparison of endoscopic findings in horses with and without clinical signs. Equine Vet J Suppl. 1989; 7:68-72. doi:10.1111/j.2042-3306.1989.tb05659.
27. Hammond C J, Mason D K, Watkins K L. Gastric ulceration in mature thoroughbred horses. Equine Vet J. 1986 July; 18(4):284-287.
28. Sykes B W, Bowen M, Habershon-Butcher J L, Green M, Hallowell G D. Management factors and clinical implications of glandular and squamous gastric disease in horses. J Vet Intern Med. 2019; 33(1):233-240. doi:10.1111/jvim.15350
29. Vatistas N J, Snyder J R, Carlson G, et al. Cross-sectional study of gastric ulcers of the squamous mucosa in thoroughbred racehorses. Equine Vet J Suppl. 1999; 29:34-39. doi:10.1111/j.2042-3306.1999.tb05166.
30. Murray M J, Schusser G F, Pipers F S, Gross S J. Factors associated with gastric lesions in thoroughbred racehorses. Equine Vet J. 1996; 28(5):368-374. doi:10.1111/j0.2042-3306.1996.tb03107.
31. Pagan J D, Mulvey E, O'Neill K, Ireland N, Davies M. Intensity and distance of exercise during training in advanced three-day-event horses and Thoroughbred racehorses assessed using KER ClockIt Race smartphone applications. Abstract in: Proceedings of the Equine Science Society. Equine Science Society. 2017; 52:67.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of modulating fatty acid profiles in a horse, comprising administering to the subject an effective amount of a composition including a combination of gamma linolenic acid (GLA), docosahexaenoic acid (DHA), and eicosapentaenoic acid (EPA).

2. The method of claim 1, wherein the composition comprises about 5% w/w to about 25% w/w GLA, and about 5% w/w to about 25% w/w of a mixture of DHA and EPA.

3. The method of claim 1, wherein administering the composition increases an amount of EPA, DHA, GLA, and/or dihomo-gamma-linolenic acid (DGLA) in a biological sample obtained from the horse.

4. The method of claim 3, wherein the biological sample comprises plasma or red blood cells.

5. The method of claim 4, wherein the biological sample comprises red blood cells, and wherein the EPA, DHA, GLA, and/or DGLA is incorporated into the cell membranes of the red blood cells.

6. The method of claim 1, wherein administering the composition comprises administering an amount sufficient to increase an amount of GLA and/or DGLA in the horse.

7. The method of claim 1, wherein administering the composition comprises administering an amount sufficient to reduce an amount of or incidence of gastric ulcers, airway inflammation, or joint inflammation in the horse.

8. The method of claim 1, wherein administering the composition comprises administering an amount of the composition sufficient to provide a daily intake of about 1 g/d to about 10 g/d GLA and about 5 g/d to about 15 g/d of a mixture of DHA and EPA.

* * * * *